US006491724B1

(12) United States Patent
Ferree (10) Patent No.: US 6,491,724 B1
(45) Date of Patent: Dec. 10, 2002

(54) SPINAL FUSION CAGE WITH LORDOSIS CORRECTION

(76) Inventor: Bret Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 09/454,908

(22) Filed: Dec. 3, 1999

Related U.S. Application Data (60) Provisional application No. 60/148,913, filed on Aug. 13, 1999.

(51) Int. Cl.[7] ................................................. A61F 2/44
(52) U.S. Cl. .................................................. 623/17.11
(58) Field of Search ........................... 623/17.11–17.16

(56) References Cited

U.S. PATENT DOCUMENTS

| 4,904,261 A | | 2/1990 | Dove et al. .................... 623/17 |
| 5,263,953 A | | 11/1993 | Bagby .......................... 606/61 |
| 5,425,772 A | * | 6/1995 | Brantigan ................. 623/17.11 |
| 5,554,191 A | | 9/1996 | Lahille et al. ................. 623/17 |
| 5,609,635 A | | 3/1997 | Michelson .................... 623/17 |
| 5,643,329 A | | 7/1997 | Solomonow et al. ......... 607/43 |
| 5,653,763 A | | 8/1997 | Errico et al. .................. 623/17 |
| 5,776,196 A | | 7/1998 | Matsuzaki et al. ............ 623/17 |
| 5,782,919 A | | 7/1998 | Zdeblick et al. .............. 623/17 |
| 5,865,847 A | | 2/1999 | Kohrs et al. .................. 623/17 |
| 5,865,848 A | * | 2/1999 | Baker ....................... 623/17.11 |
| 5,885,287 A | | 3/1999 | Bagby .......................... 606/61 |
| 5,888,227 A | | 3/1999 | Cottle .......................... 623/17 |
| 5,893,890 A | * | 4/1999 | Pisharodi ................. 623/17.11 |
| 5,895,427 A | | 4/1999 | Kuslich et al. ................ 623/17 |
| 5,897,593 A | | 4/1999 | Kohrs et al. .................. 623/17 |
| 5,906,616 A | | 5/1999 | Pavlov et al. ................. 606/61 |
| 5,989,291 A | * | 11/1999 | Ralph et al. .............. 623/17.13 |
| 6,019,793 A | * | 2/2000 | Perren et al. ............. 623/17.11 |
| 6,066,325 A | * | 5/2000 | Wallace et al. ............. 424/400 |
| 6,102,950 A | * | 8/2000 | Vaccaro .................... 623/17.11 |
| 6,110,210 A | * | 8/2000 | Norton et al. ........... 623/17.16 |
| 6,117,174 A | * | 9/2000 | Nolan ....................... 623/17.11 |
| 6,143,032 A | * | 11/2000 | Schafer et al. ........... 623/17.11 |
| 6,179,875 B1 | * | 1/2001 | Von Strempel .......... 623/17.16 |
| 6,190,414 B1 | * | 2/2001 | Young et al. ............. 623/17.15 |
| 6,193,757 B1 | * | 2/2001 | Foley et al. ............. 623/17.16 |
| 6,206,922 B1 | | 3/2001 | Zdeblick et al. ......... 623/17.11 |
| 6,245,108 B1 | * | 6/2001 | Biscup ..................... 623/17.11 |

* cited by examiner

Primary Examiner—David H. Willse
Assistant Examiner—Suzette J. Jackson
(74) Attorney, Agent, or Firm—Gifford, Krass, Groh, Sprinkle, Anderson & Citkowski, PC (57) ABSTRACT

Intervertebral cages, and methods of introducing the same, require few, if any, structural components within the cage itself, thereby providing a maximum volume for bone-graft filler. Cages according to the invention may passively expand to fill a volume within the disk space, or active expansion means may be provided. In terms of a passive expansion, at least a portion of the frame may be composed of a shape-memory material, causing the cage to naturally expand from the compressed to the expanded state once the cage is positioned within the intervertebral space. In either case, locking means are provided to maintain the shape of the cage once in position. An alternative embodiment includes first and second components, each having a compressed state which consumes a compressed volume associated with insertion of the component into an intervertebral space, and an expanded state which consumes a greater volume when the component is positioned within the intervertebral space. In terms of an active expansion, an externally accessible mechanism may be used to increase the anterior height once the cage is positioned within the intervertebral space. In all embodiments, connection means may be provided for interconnecting a plurality of cages together within the same intervertebral space.

13 Claims, 6 Drawing Sheets

SPINAL FUSION CAGE WITH LORDOSIS CORRECTION

REFERENCE TO RELATED APPLICATION

This application claims priority from U.S. provisional application Serial No. 60/148,913, filed Aug. 13, 1999, the contents of which are incorporated herein by reference.

FIELD OF THE INVENTION

This invention relates generally to spinal surgery and, in particular, to spinal cages of the type used in fusing adjacent vertebrae.

BACKGROUND OF THE INVENTION

Eighty-five percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treatment of patients with spinal disorders plus the patient's lost productivity is estimated at 25 to 100 billion dollars annually.

Seven cervical (neck), 12 thoracic, and 5 lumbar (low back) vertebrae form the normal human spine. Intervertebral discs reside between adjacent vertebra with two exceptions. First, the articulation between the first two cervical vertebrae does not contain a disc. Second, a disc lies between the last lumbar vertebra and the sacrum (a portion of the pelvis).

Motion between vertebrae occurs through the disc and two facet joints. The disc lies in the front or anterior portion of the spine. The facet joints lie laterally on either side of the posterior portion of the spine. The osseous-disc combination of the spine coupled with ligaments, tendons, and muscles are essential for spine function. The spine allows movement (flexion, lateral bending, and rotation), supports the body, and protects the spinal cord and nerves.

The disc changes with aging. As a person ages the water content of the disc falls from approximately 85 percent at birth to 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears. Disc herniation can also cause arthritis of the facet joints which, in turn may cause back pain.

The problems created by disc degeneration, facet arthritis, and other conditions such as spondylolysis, spondylolisthesis, scoliosis, fracture, tumor, or infection are frequently treated by spinal fusion. Such problems may include pain in the back or legs, nerve injury, risk of future nerve injury, or spinal deformity. The goal of spinal fusion is to successfully "grow" two or more vertebrae together. To achieve this, bone from the patient's body (spine or iliac crest) or from cadavers, is grafted between vertebrae. Alternatively, bone graft substitutes, such as hydroxy appetite and bone morphogenetic protein, may be used. The bone graft is placed between the vertebrae in the disc space and/or over the posterior elements of the vertebrae (lamina and transverse processes). The surgeon scrapes the vertebrae to create bleeding. Blood flows into the bone graft. The scraped bone, blood clot (hematoma), and the bone graft simulates a fracture. As the patient heals, the "fracture" causes the vertebrae to be fused and heal together.

Spinal instrumentation, including cages, is placed onto or into the spine to immobilize the vertebrae that are going to be fused. Immobilization leads to a higher fusion rate and speeds a patient's recovery by eliminating movement. Existing cages are typically hollow metal or carbon fiber devices placed into the disc space. Often cages have treads, grooves, teeth or spikes that engage the vertebral endplates. The hollow center is filled with bone graft. The sides of the cages adjacent to the vertebral endplates contain holes to allow bone growth from one vertebrae through the cage to the adjacent vertebra. The bone graft acts as a bridge for bone growth. Cages immobilize the vertebrae and maintain the separation between the vertebrae, a function of the former disc material. Cages are placed into the disc space after excising a portion of the disc annulus and most of the nucleus. One or two cages may be inserted at each level.

Cages may be placed into the disc space from an anterior or a posterior approach to the spine. Cages may be combined with rods, screws, hooks, or plates. Combining cages with other instrumentation yields a stiffer construct and presumably increases the chance of a successful fusion. If cages are placed from an anterior approach (through the abdomen) the patient must undergo surgery through a second incision over the back (posterior approach) if the surgeon wants to also insert rods and screws. To avoid two incisions and increased patient morbidity, many surgeons prefer to insert the cages from a posterior approach. Rods and screws can be added through the same incision.

The cages currently available for insertion from a posterior approach have a few important weaknesses. Since most cages are inserted into the disc space in their final size and shape, the cages must be large enough to extend from vertebra-to-vertebra. Furthermore, the cages must be wide enough to provide stability and provide adequate surface area for the vertebrae to "grow" together. Large cages inserted posteriorly risk nerve injury (from retracting the nerves to insert the cage or the edge of the cage during insertion) or extensive bone removal. A portion of the vertebra (lamina, a portion of the facet(s) and/or the entire facet(s)) is removed to allow cage insertion. Large cages require more bone removal. Some surgeons remove one or both facet joints to safely insert the cage or cages. Removal of the facet joints destabilizes the spine, which may lead to cage migration and/or pseudoarthrosis (failure of the bone to heal). Either complication may require the patient to undergo additional surgery. Revision procedures are more difficult after removal of the facet joints.

Most of the cages inserted posteriorly have parallel superior and inferior surfaces. The endplates of the vertebrae form the superior and inferior limits of the disc space. The endplates are not typically parallel in the lumbar spine. Generally, the endplates become closer together as one proceeds toward the posterior portion of the disc space. This alignment creates the normal anterior to posterior curvature of the lumbar spine known as lordosis. Cages with parallel superior and inferior surfaces either fit tightly posterior and loosely anteriorly, or require removal of additional endplate posteriorly. Alternatively, the vertebrae can be fused without lordosis. None of these choices are ideal.

SUMMARY OF THE INVENTION

This invention improves upon the existing art by providing intervertebral cages, and methods of introducing the same, which require few, if any, structural components within the cage itself, thereby providing a maximum volume for bone-graft filler materials.

According to a first preferred embodiment, a cage according to the invention features a compressed state associated with insertion of the cage into an intervertebral space having an anterior height which is less than or equal to the posterior height, and an expanded state, wherein the anterior height is greater than the posterior height to account for lordosis. Means are further provided for locking the cage into the expanded state once the cage is positioned within the intervertebral space. Such means preferably includes a ratchet mechanism associated with the anterior portion which locks the cage into desired wedge configuration.

Cages according to the invention may passively expand to fill a volume within the disk space, or active expansion means may be provided. In terms of a passive expansion, at least a portion of the frame may be composed of a shape-memory material, causing the cage to naturally expand from the compressed to the expanded state once the cage is positioned within the intervertebral space. Alternatively, superior and inferior members may be attached to the posterior portion so as to form a spring, which causes the cage to naturally expand from the compressed to the expanded state. The superior and inferior surfaces preferably include protrusions for frictionally engaging with vertebral endplates defining the disk space.

In terms of an active expansion, an intervertebral cage according to the invention may include an externally accessible mechanism operative to increase the anterior height once the cage is positioned within the intervertebral space. For example, such a mechanism may include a slug positioned on a threaded rod which moves posterior to anterior when the rod is rotated. An alternative embodiment includes first and second components, each having a compressed state which consumes a compressed volume associated with insertion of the component into an intervertebral space, and an expanded state which consumes a greater volume when the component is positioned within the intervertebral space. In this case, the shape of the components is such that the first component when expanded leaves a gap which is closed by the second component when expanded. In all embodiments, connection means may be provided for interconnecting a plurality of cages together within the same intervertebral space.

DETAILED DESCRIPTION OF THE INVENTION

Figure 1:
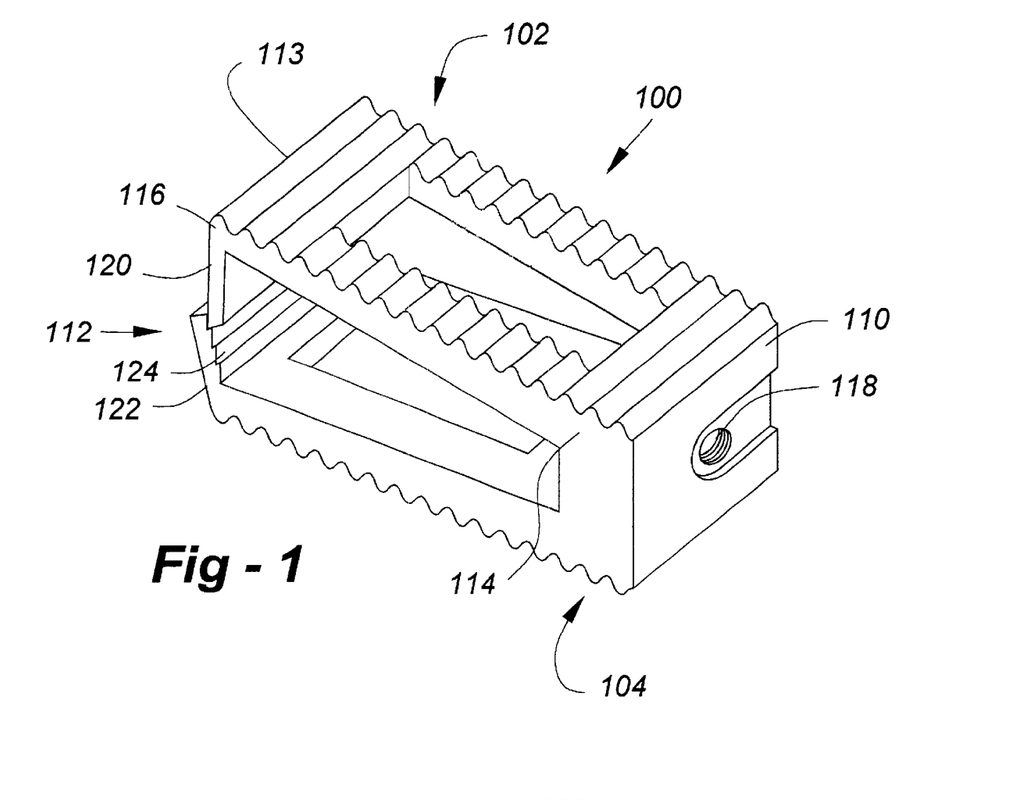
FIG. 1 is a drawing which shows a preferred expandable cage according to the invention without bone-graft filler.
Figure 2:
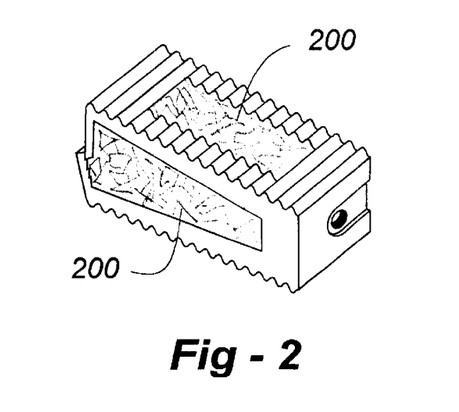
FIG. 2 is a drawing which shows the cage of FIG. 1 including bone-graft filler.

FIG. 1 illustrates, from an oblique perspective, a spinal cage 100 according to the invention prior to the introduction of bone graft material. FIG. 2 is a drawing of the device of FIG. 1, but with bone graft material 200 introduced within the interior of the cage. The device overall assumes the form of a generally rectangular cage having apertured upper and lower members with superior and inferior surfaces 102 and 104, respectively, and open sides. The device as shown is oriented with its posterior portion 110 facing generally outwardly and to the right of the page, and with the anterior portion 112 facing generally into and leftward on the page. The superior and inferior surfaces preferably include grooves 113, as shown, or alternative surfacing to better engage with the endplates of the adjacent vertebrae for long-term stability. The superior and inferior surfaces may also be convex to better conform to endplate concavity. Note further that the either or both of the upper and lower member may be wider posteriorly (i.e., at 114) relative to the anterior thickness (i.e., at 116) to provide added strength in compression at the back of the spine. A screw hole 118 is preferably provided for temporary coupling to an inserter. The screw hole is also preferably recessed to accommodate a transverse connector bar without rotation, as described further below.

When the device is implanted within the intervertebral space, the anterior sections of the upper and lower members are passively or actively expanded as described below to fill the space between the adjacent vertebrae in a manner consistent with lordosis at that section of the spine. In the preferred embodiment, the anterior portion 112 includes mating members 120 and 122 with teeth 124 or other features to form a locking or ratchet mechanism, as shown. Whatever apparatus is used, the purpose is to maintain the height of the anterior portion of the cage at a desired level consistent with lordosis upon installation.

Figure 3:
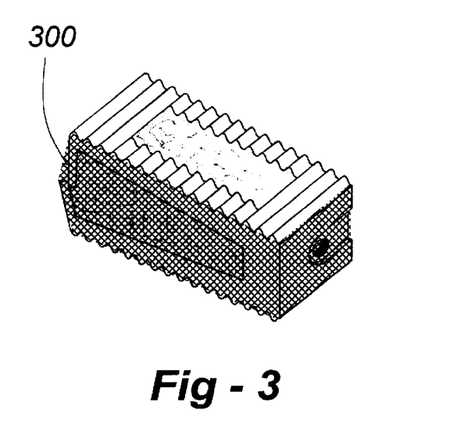
FIG. 3 is a drawing of the cage of FIGS. 1 and 2 illustrating the use of a radiolucent sleeve surrounding the cage.
Figure 4:
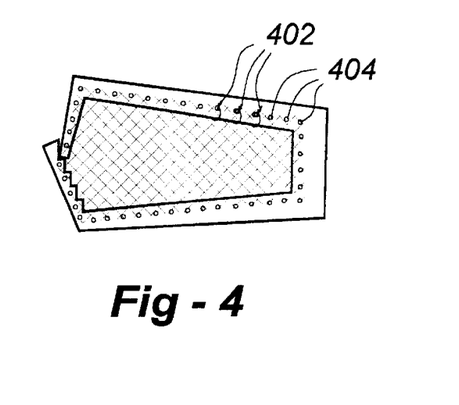
FIG. 4 is a side-view drawing illustrating the way in which a mesh may be attached to the side openings of an expandable cage.
Figure 5A:
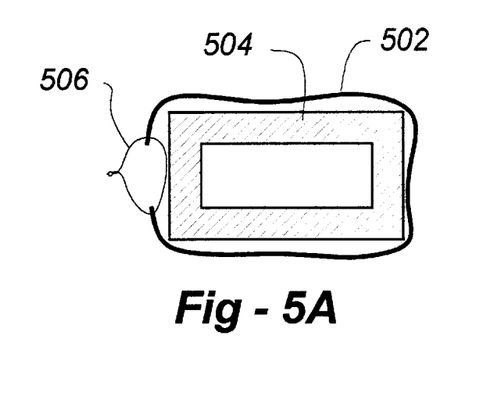
FIG. 5A is a drawing which shows how a screen may be sutured around a cage.
Figure 5B:
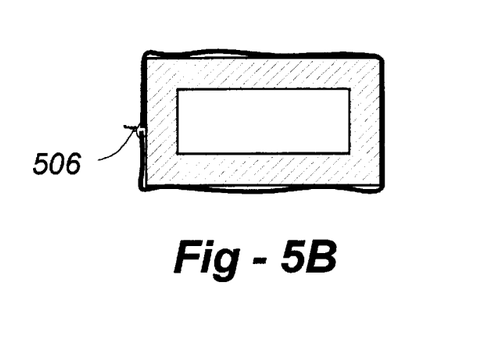
FIG. 5B is a drawing which shows the sutured sleeve tightened around the cage.
Figure 6A:
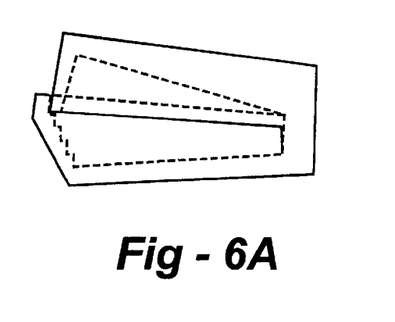
FIG. 6A is a side-view drawing which shows how superior and inferior members may cooperate to enclose a cage volume.
Figure 6B:
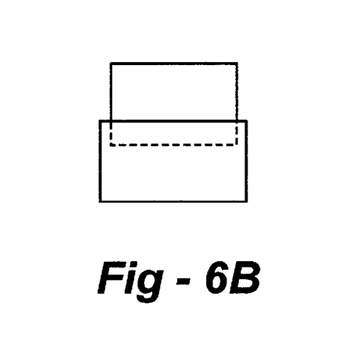
FIG. 6B is an end-view drawing of the configuration of FIG. 6A.
Figure 7:
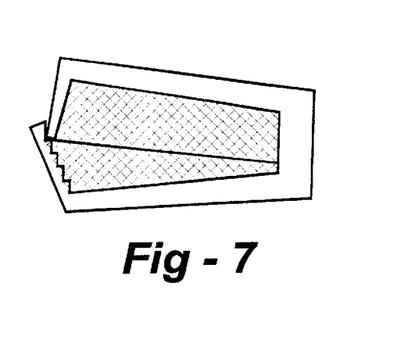
FIG. 7 is a drawing which shows how mesh as opposed to solid sides may be used in an overlapping structure.

As shown in FIG. 3, a radiolucent mesh sleeve 300 is also preferably installed around the cage when filled with bone graft material. FIG. 4 is a side-view drawing which illustrates a preferred technique for attaching a radiolucent screen to the side of the cage. Preferably the screen, of a nylon mesh construction, is attached to the cage through the use of a nylon suture 402 using a plurality of spaced-apart holes 404 positioned around the side opening. Instead of, or in conjunction with, the screen attachment just described with reference to FIG. 5A, a mesh sleeve or bag 502 may wrapped around the cage 504 with the edges or opening sewn together, as shown at 506. FIG. 5B is a drawing which shows the sleeve or bag tightened around the cage. As opposed to the use of a screen material, the cage may be constructed such that a portion of the top or bottom half sleeves over the other half, thereby closing the side openings when the two halves are put together. Such an arrangement is shown in FIGS. 6A and 6B. As opposed to solid side members, overlapping mesh panels may be used, as shown in FIG. 7.

Either active or passive means may be used to expand the cage when placed. In terms of passive approaches, the cage itself is preferably fashioned as a spring or constructed of a shape-memory material allowing the device to be compressed for implantation through a relatively small opening, but, once in place, the material naturally returns to its pre-implantation configuration. With respect to the preferred embodiment of a cage with lordosis correction, the device relaxes or expands into a wedge which is taller anteriorly relative to its posterior height. As such, the device may be introduced with the height of the anterior section of the device being less than or equal to the height of the posterior section but, once in place and with the device resuming its pre-installation shape, the anterior height is greater than the posterior height.

Various materials may be utilized as part of a cage which passively expands into a desired shape according to the invention. For example, a list of candidate materials would include stainless steel, cobalt-chromium-molybdenum alloys, titanium, carbon reinforced polymers, shape memory alloys, materials commonly used for commercial and industrial springs, and nylon or other fiber or polymer materials used for the radiolucent screen or mesh sleeve. In terms of carbon-reinforced polymers, those materials referenced in U.S. Pat. No. 5,192,327, the entire contents of which is incorporated herein by reference, may be used, which include polyetherether ketone, (polyether ketone, ether ketone, and ketone), polycarbonate, polypropylenes, polyethyelene and polysulfone type plastic materials with or without glass or carbon fibers. In terms of shape-memory alloys, those materials set forth in U.S. Pat. No. 5,954,725, the entire contents of which are incorporated herein by reference, may be used, including, but not limited to alloys of copper and zinc, nickel titanium, silver and cadmium, and other metals and materials, including Nitinol™).

Figure 8A:
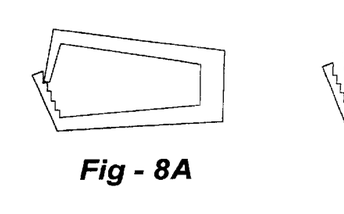
FIG. 8A is a drawing which shows a shape-memory cage prior to compression for introduction within an intervertebral space.
Figure 8B:
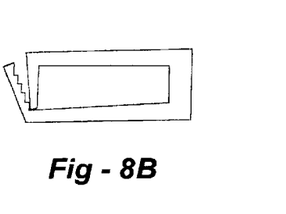
FIG. 8B shows the device of FIG. 8A having been compressed for insertion through an annular wall.
Figure 8C:
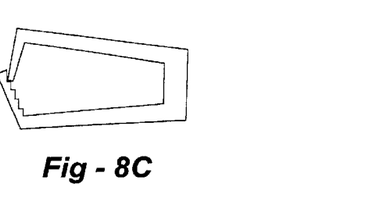
FIG. 8C is a drawing which shows the device of FIGS. 8A and 8B re-expanded to fill an intervertebral in a manner consistent with lordosis.

As discussed above, apparatus is provided at the anterior portion of the device to lock the anterior height once a desired wedge shape is achieved. FIG. 8A shows a device according to the invention having a shape memory configuration which will be naturally resumed following a temporary compression. This temporary compression is shown in FIG. 8B, wherein the anterior portion is compressed into a generally rectangular shape for introduction into the intervertebral space. Following such introduction, the device resumes it memorized shape, as shown in FIG. 8C. Once a desired wedge configuration has been achieved, the locking mechanism at the anterior portion of the device engages once the desired anterior height has been achieved, thereby preventing further compression of the cage overall.

Figure 8D:
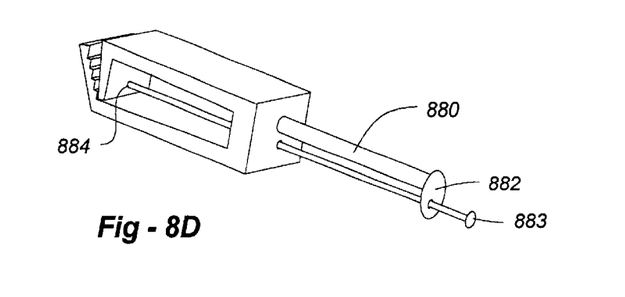
FIG. 8D is a drawing which shows one way in which an elongated member may be used to hold a cage according to the invention in a collapsed state during introduction of the device into an intervertebral space.

FIG. 8D illustrates, from an oblique perspective, instrumentation which may be used to introduce a cage according to the invention into an intevertebral space in a collapsed condition. Such instrumentation may include a central elongated member 880, having a distal end attached to the posterior portion of the cage as through the threaded hold 118 shown in FIG. 1. The proximal end of the member 880 would include in this case a plate 882 having an aperture which receives a second elongated member 883. The second member 883 extends through the posterior section of the device, and attaches one of the interlocking forward members at 884. Using such an instrument, the surgeon would pull back on rod 883 while holding rod 880, allowing the anterior portion of the cage to be non-ratcheted and reduced in size. Following introduction of the cage into the intervertebral space, rod 883 may be removed or pushed forward, depending upon cage construction, causing the anterior portion to expand as appropriate and lock into ratcheting position. Following this expansion, both members 880 and 883 would be removed, leaving only the cage in place. It is noted that such a system is applicable not only to the embodiment of the type shown in FIG. 1, but also to those depicted in FIGS. 11 and 12.

Figure 9A:
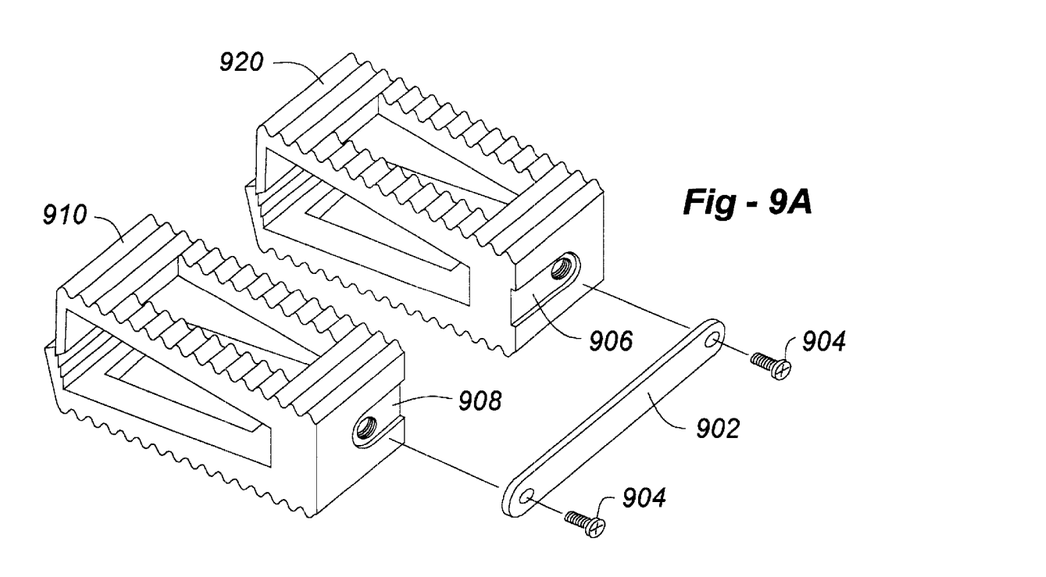
FIG. 9A is an oblique drawing which shows two cages being interconnected with a transverse bar.
Figure 9B:
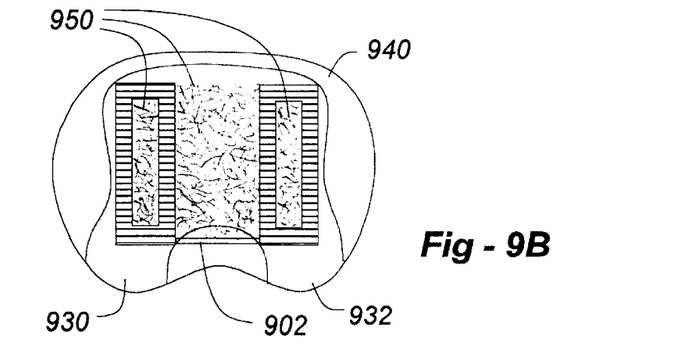
FIG. 9B is a head-to-foot drawing showing the interconnected cages of FIG. 9A with bone graft material filling the cages in the space between the cages.

FIGS. 9A and 9B illustrate the way in which two devices according to the invention may be interlocked using a transverse connector 902 and fasteners such as screws 904. The transverse connector 904 fits into recesses 906 and 908 which are preferably provided on the posterior surfaces of the devices, to prevent rotation and provide a more planar posterior surface overall, as discussed above. Note that the devices 910 and 920 may be entirely independent of one another in terms of their final shape, such that they need not assume the same wedge size once implanted, but rather, may be different in accordance with spinal defects and other aspects of patient physiology. FIG. 9B is a top view of two devices 910 and 920 installed within the intervertebral space, having been joined with a transverse connector 902. Openings 930 and 932 in the wall of the annulus 940 show where the devices were installed medially and laterally. FIG. 9B also shows how bone graft material 950 is preferably introduced throughout the intervertebral space, not only within the cages themselves, but in between the cages, as shown.

Figure 10A:
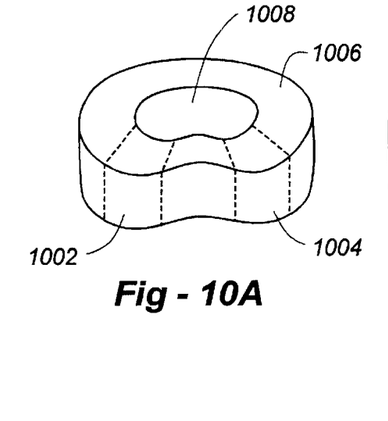
FIG. 10A is a drawing which begins a sequence of illustrations showing how two cages may be introduced side-by-side within an intervertebral space.
Figure 10B:
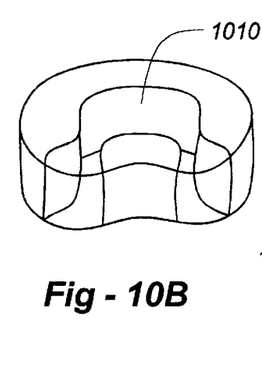
FIG. 10B is a drawing which shows the nucleus having been evacuated from the disc space.
Figure 10C:
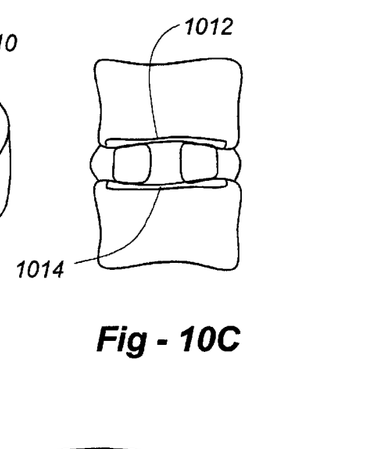
FIG. 10C shows how the vertebral endplates are scraped prior to insertion of cages.

FIG. 10A begins a sequence of drawings which help to illustrate how a pair of spinal cages according to the invention are implanted and adjusted. FIG. 10A illustrates, in simplified schematic form, the location of openings formed 1002 and 1004 in the annulus 1006, thereby gaining access to the nucleus 1008. FIG. 10B is a drawing which shows the nucleus having been evacuated from space 1010. FIG. 10C is a posterior-anterior view in partial cross-section illustrating how the end plates of the adjacent vertebrae are scraped at 1012 and 1014 using tools inserted through the holes in the annulus fibrosis.

Figure 10D:
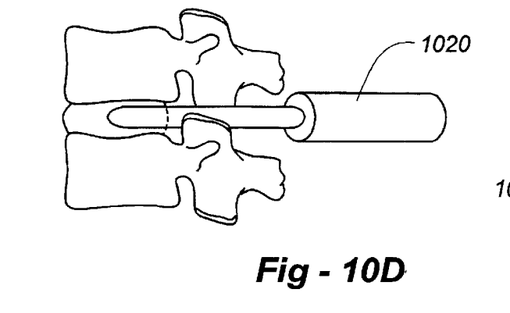
FIG. 10D illustrates the use of a distracter tool to hold the vertebrae apart for introduction of an adjacent cage.
Figure 10E:
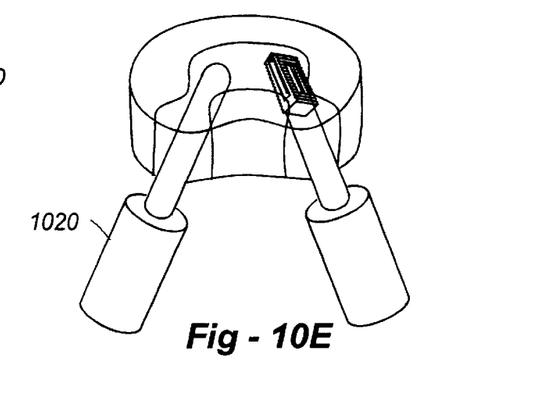
FIG. 10E how the adjacent cage is introduced with the distracter in place.
Figure 10F:
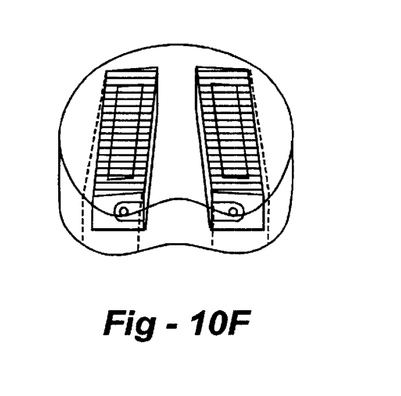
FIG. 10F illustrates two cages side-by-side within an intervertebral space but not connected together.
Figure 10G:
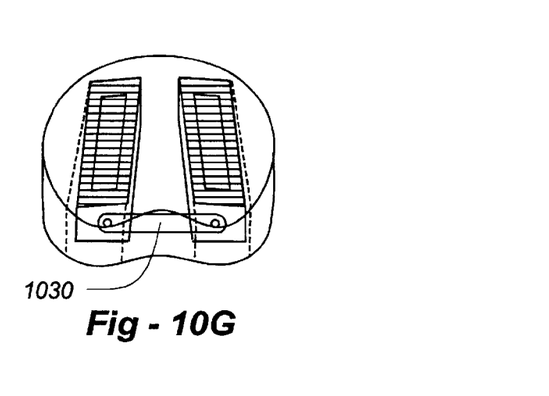
FIG. 10G illustrates the way in which medial and lateral cages may be connected with a transverse bar.

In FIG. 10D, a distracter tool 1020 is introduced medially or laterally through one of the holes in the annulus, so as to separate the adjacent vertebrae a desired amount, as determined through existing surgical techniques. With the distracter in place, a cage according to the invention is inserted into the other opening in the annulus, as shown in FIG. 10E. FIG. 10F is a drawing which shows two cages in place without a transverse connector, and FIG. 10G is a drawing which shows the cages of FIG. 10F coupled together using a transverse connector 1030.

Figure 11A:
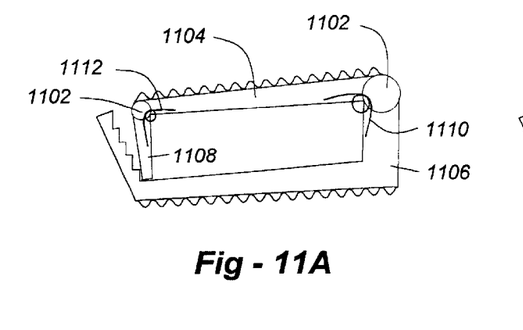
FIG. 11A illustrates the use of hinges as opposed to a shape-memory or spring configuration.
Figure 11B:
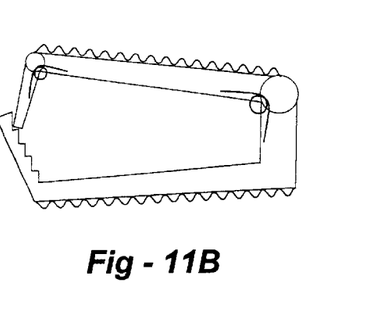
FIG. 11B shows the device of FIG. 11A ratcheted into a preferred shape orientation.

As opposed to the entire use of shape-memory material, hinges may be used instead of, or in conjunction with shape-memory elements. For example, as shown in FIG. 11A, one or more hinges 1102 may be provided between the upper member 1104 and posterior portion 1106 and/or the upper member 1104 and a portion of the ratchet mechanism 1112, as shown. Springs 1110 and/or 1112 may also be provided to bias the various members so as to expand appropriately upon introduction in to the disk space. FIG. 11A shows the device in the collapsed state, such that the anterior portion is actually reduced in height as compared to the posterior portion, whereas, in the expanded device, the anterior portion is equal to, or greater than, the posterior portion as a function of lordosis, as shown in FIG. 11B.

Figure 12A:
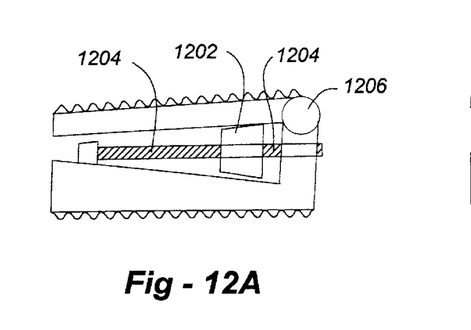
FIG. 12A is a drawing which shows how active means in the form of a threaded rod and slug may be used to expand a cage according to the invention.
Figure 12B:
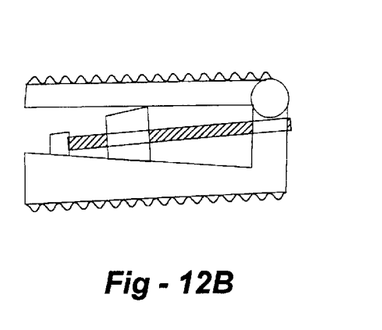
FIG. 12B shows the cage of FIG. 12A having been expanded.

As shown in FIG. 12A, adjustment mechanisms may also be provided according to the invention to achieve a desired wedge configuration one the cage is in place using an externally applied adjustment force. In FIG. 12A, the cage is shown in a collapsed state with a slug 1202 on a threaded rod 1204 being set back from the anterior region, allowing the height of the device to be compressed from front to back, as shown. By turning the threaded rod 1204, the slug 1202 is moved to posterior to anterior, with the surfaces of the slug bearing against the lower and upper members, causing the upper member to hinge at point 1206, and move upwardly, as shown in FIG. 12B, to assume a desired wedge-shaped orientation following introduction into the intervertebral disc space.

Figure 13A:
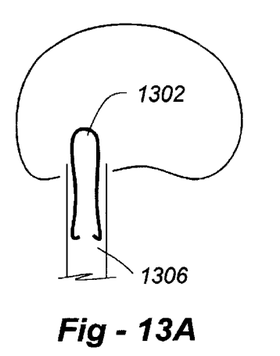
FIG. 13A is a drawing which begins a sequence of diagrams showing a two-part intervertebral cage and method of introducing the components into a disc space.
Figure 13B:
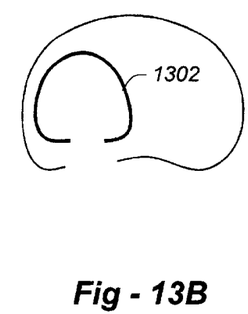
FIG. 13B illustrates a first component having been inserted and expanded.

FIG. 13A is a drawing viewed from head to foot of an alternative embodiment of the invention utilizing a shape-memory cage which is constructed within the disc space, but which does not necessarily provide for lordosis correction. Each cage is preferably constructed of an anterior shape memory component 1302 and a posterior component 1304, also preferably constructed in the form of a shaped-memory device. FIG. 13A illustrates the anterior component 1302 being inserted according to this embodiment. FIG. 13B shows the device 1302 in its expanded or relaxed configuration, assuming the general form of a "C" with the opening of the C being oriented posteriorly when in place.

Figure 13C:
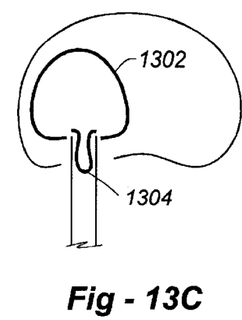
FIG. 13C shows the use of an inserter to install the second component of this two-part system.
Figure 13D:
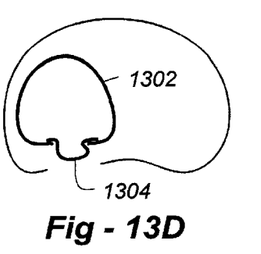
FIG. 13D shows the second component expanded to fill a gap in the first part.
Figure 13E:
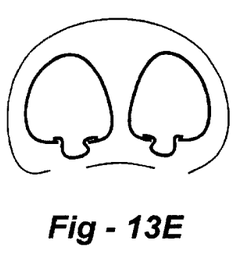
FIG. 13E illustrates two cages side-by-side according to this aspect of the invention.
Figure 13F:
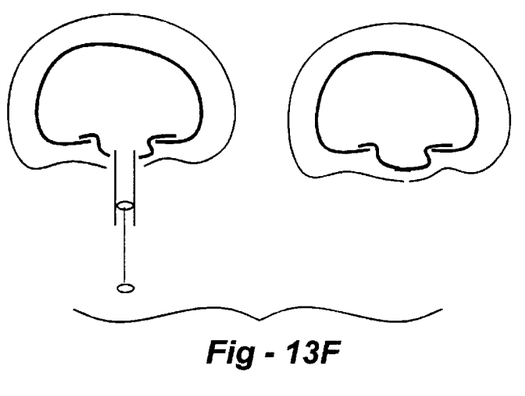
FIG. 13F shows how one of the components preferably includes an aperture through which bone graft material is inserted.
Figure 13G:
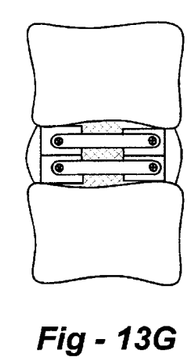
FIG. 13G is a drawing which shows two cages inserted from an anterior approach with two transverse connectors and a radiolucent screen holding bone graft between the cages.

FIG. 13C shows the posterior component 1304 in a collapsed state and being pushed outwardly through the distal opening of an inserter 1306. FIG. 13D is a top-view drawing showing the inserter removed, allowing the anterior shape-memory component to relax and resume a configuration which blocks the opening of the C-shaped anterior component. The procedure is then repeated for the other side, resulting in adjacent assemblies. FIG. 13E is a drawing which shows two cages according to the invention placed side by side within a common disk space, each cage having separate anterior and posterior components. Preferably, the posterior components include an aperture through which bone-graft material may be introduced into the cages, then plugged once filled, as shown in FIG. 13F. As with the generally rectangular cage described with reference to the preferred embodiment of the invention, the adjacent assemblies may be joined using one or more transverse connectors, as shown in FIG. 13G, and the space between the assemblies may be filled with additional bone-graft material, thereby substantially filled the space between the vertebral endplates.

Figure 14:
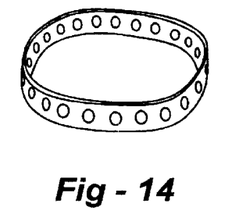
FIG. 14 is a drawing of yet a further alternative cage according to the invention, in this case assuming the form of a collapsible, expandable strip of material without optional multiple perforations for the introduction of bone graft material.

According to a different configuration, as an alternative to a two-part collapsible strip system of the type just described, a single collapsible/expandable strip may be used, as shown in FIG. 14. Preferably, the device would be collapsed into an elongated shape for introduction through an inserter, after which, being composed of a spring or shape-memory material, would expand or relax into a larger volume. Preferably, such a device would include a plurality of apertures, as shown in FIG. 14, such that one or more may be used for the introduction of bone graft material following implantation and expansion.

I claim:

1. An intervertebral cage, comprising:
    a rigid frame having anterior and posterior portions, superior and inferior surfaces, and two opposing sides;
    the thickness of the frame between the superior and inferior surfaces in the anterior portion defining an anterior height, and the thickness of the frame between the superior and inferior surfaces in the posterior portion defining a posterior height;
    a connector associated with the posterior portion facilitating insertion of the frame into an intervertebral space using a posterior approach;

the frame having a compressed state associated with insertion of the frame into an intervertebral space, wherein the anterior height is less than or equal to the posterior height, and an expanded state, wherein the anterior height is greater than the posterior height to account for lordosis; and a mechanism for locking the cage into the expanded state once the frame is positioned within intervertebral space.

2. The intervertebral cage of claim 1, wherein the means for locking the frame into the expanded state includes a ratchet mechanism associated with the anterior portion.

3. The Intervertebral cage of claim 1, wherein the interior volume of the frame is substantially unoccupied to receive bone graft material.

4. The intervertebral cage of claim 1, wherein at least a portion of the frame is composed of a shape-memory material causing the frame to naturally expand from the compressed to the expanded state once the frame is positioned within the intervertebral space.

5. The intervertebral cage of claim 1, wherein the superior and inferior surfaces are attached to the posterior portion so as to form a spring which causes the cage to naturally expand from the compressed to the expanded state once the cage is positioned within the intervertebral space.

6. The intervertebral cage of claim 1, wherein the superior and inferior surfaces include protrusions for frictionally engaging with vertebral endplates defining the disk space.

7. The intervertebral cage of claim 1, wherein one or both of the superior and inferior surfaces are convex.

8. The intervertebral cage of claim 1, wherein one or both of the superior and inferior surfaces are hinged to the posterior portion.

9. The intervertebral cage of claim 1, wherein the mechanism for locking the cage into the expanded state includes one or two anterior members hinged to one or both of the superior and inferior surfaces, respectively.

10. The intervertebral cage of claim 1, further including a posteriorly accessible mechanism operative to increase the anterior height once the cage is positioned within the intervertebral space.

11. The intervertebral cage of claim 10, wherein the posteriorly accessible mechanism includes a slug positioned on a threaded rod which moves back and forth posterior to anterior when the rod is rotated.

12. The intervertebral cage of claim 1, further including a radiolucent screen covering at least the open sides of the cage.

13. The intervertebral cage of claim 1, further including a connector associated with the posterior portion for interconnecting a plurality of the frames together within the same intervertebral space.

* * * * *